(12) United States Patent
Ray et al.

(10) Patent No.: US 7,345,176 B2
(45) Date of Patent: Mar. 18, 2008

(54) PROCESS FOR CONVERSION OF CYANOPYRIDINES TO NICOTINAMIDES AND CATALYST THEREFOR, PROCESS FOR PREPARING SAID CATALYST

(75) Inventors: Subhash Chandra Ray, Jharkhand (IN); Baldev Singh, Jharkhand (IN); Hiralal Prasad, Jharkand (IN); Prodyot Kumar Sarkar, Jharkhand (IN); Pashupati Dutta, Jharkhand (IN); Shyam Kishore Roy, Jharkhand (IN); Anup Kumar Bandyopadhyay, Jharkhand (IN); Raja Sen, Jharkhand (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 11/124,142

(22) Filed: May 9, 2005

(65) Prior Publication Data

US 2005/0209461 A1    Sep. 22, 2005

Related U.S. Application Data

(63) Continuation of application No. 10/392,388, filed on Mar. 20, 2003, now abandoned.

(51) Int. Cl.
    *C07D 213/81*    (2006.01)
(52) U.S. Cl. .................................... 546/317
(58) Field of Classification Search ................ 546/317
    See application file for complete search history.

(56) References Cited

U.S. PATENT DOCUMENTS 3,957,804 A * 5/1976 Ishioka et al. ............... 546/317

FOREIGN PATENT DOCUMENTS

GB      1 133 013 A     11/1968
GB      1 351 530 A     5/1974
JP      51006672        3/1976
WO      WO 96 16039 A   5/1996

OTHER PUBLICATIONS

Breno et al., "Organometallic Chemistry, etc." Organometallics 2003, 22, 1203-1211.*
Hirayama et al., "Hydration of nitriles, etc.," CA 120: 163480 (1993).*
Ghaffar et al. I, "A New Homogeneous Platinum, etc.," Tetrahedron Letters, 36 (47), oo 8657-8660 (1995).*
Ghaffar et al. II, "The catalytic hydration, etc.," Journal of Moleular Catalysis A: Chemical 160 (2000) 249-261.*
Roy et al., "The catalyzed hydration, etc.," Journal of the Indian Chemical Society (1988), 57(2), 195-8.*
Misra et al., "Studies on the catalytic, etc.," Journal of the Indian Chemical Society (1979), 56(2), 208-9.*
Roy et al; "The Catalyzed Hydration of Nitriles to Amides", Journal of the Indian Chemical Society (1980), 57(2), 195-8; XP-002251248.
Misra et al, "Studies on the Catalytic Hydration of Cyano Compounds to Amides," Ranchi Univ., Ranchi, 834 008, India, Journal of the Indian Chemical Society (1979), 56(2), 208-9; XP-002251249.
STN Search, Chemical Abstract 126:347116, "Synthesis and ion exchange properties of various forms of manganese dioxide for cations of the I and II groups", Bartos et al.
CA 103:76789 "Study of the activity and selectivity of a supported catalyst from oxides of metals of varying valence in the oxidative ammonolysis of 3-picoline", vol. 103, p. 367, 1985.

* cited by examiner

*Primary Examiner*—Patricia L. Morris
(74) *Attorney, Agent, or Firm*—Nixon & Vanderhye, PC

(57) ABSTRACT

The present invention relates to an improved process for conversion of cyanopyridines to nicotinamides. More particularly the present invention relates to preparation of nicotinamides and isonicotinamides which finds its usage in the preparation of anti-TB drug i.e. isoniazid and as an intermediate of vitamin $B_{12}$. The present invention also relates to a process for a catalyst useful for the preparation of nicotinamide and isonicotinamide.

15 Claims, No Drawings

PROCESS FOR CONVERSION OF CYANOPYRIDINES TO NICOTINAMIDES AND CATALYST THEREFOR, PROCESS FOR PREPARING SAID CATALYST

CROSS REFERENCE TO RELATED APPLICATION

This application is a continuation of application Ser. No. 10/392,388 filed Mar. 20, 2003 now abandoned, the entire content of which is hereby incorporated by reference in this application

FIELD OF THE INVENTION

The present invention relates to an improved process for conversion of cyanopyridines to nicotinamides. More particularly the present invention relates to preparation of nicotinamides and isonicotinamides which finds its usage in the preparation of anti-TB drug i.e. isoniazid and as an intermediate of vitamin $B_{12}$. The present invention also relates to a process for a catalyst useful for the preparation of nicotinamide and isonicotinamide.

BACKGROUND OF THE INVENTION

Reference is made to Bull. Chem. Soc., Japan, Vol.-40, P-1660 (1967) wherein nickel oxide has been used as a catalyst for the hydration of 3-cyanopyridine to nicotinamide. The drawbacks are that the catalytic activity was reported to be low and the yield of nicotinamide was also low. Reference is also made to U.S. Pat. No. 4,008,241 to Gelbein et al of M/s. The Luffus Company (Bloom Field, N.J., USA) for the production of nicotinamide from 3-cyanopyridine by aqueous ammonia solution. The reaction temperature was 90-150° C., the reaction time was 4-8 hours and the ammonia concentration was 3-8 molar. The maximum conversion of 3-cyanopyridine was about 70%. The hydrolysis was also effected in the presence of ammonium nicotinate in an amount sufficient to essentially eliminate production thereof to produce a hydrolysis effluent containing nicotinamide, ammonia unconverted 3-cyanopyridine and ammonium nicotinate, at a nicotinamide selectivity of essentially 100%. Further, in this process unconverted 3-cyanopyridine and ammonia were separated from the product nicotinamide by a multi step separation process which is not cost effective and is a very difficult procedure to get the pure product. These are the main drawbacks of the above process.

Prior art also discusses the hydration of nitrites to amides. The conversion of nitriles to amides has been achieved by both chemical and biological means. Japanese Patent 93-206579, August, 1993, H. Hirayama (To Showa Denko K. K., Japan), European Patent 85-306670, Sep. 19, 1985, S. Asano and J. Kitagawa (to Mitsui Toatsu Chemicals Inc.) describe the use of modified Raney Nickel Catalyst for this reaction. WO 90/09988 A1, Sep. 17, 1990, of A. McKillop and D. Kemp. (to Interlex Chemicals, Ltd.) describes the use of alkali metal borates for this reaction U.S. Pat. No. 2,471,518, May 31, 1949 (to Pyridium Company); U.S. Pat. No. 4,721,709, Dec. 6, 1988 (to Standard Oil Company); German Patent Application 2,517,054, Apr. 17, 1975, (to Degussa Company), discuss the hydrolysis of 3-cyanopyridine in presence of sodium hydroxide. The use of magnesium oxide catalyst for this reaction are discussed in *Chemical Engineering Science*, 35, 330, 1975, by C. B. Rossa and G. B. Smith. Alkaline hydrolysis of 3-cyanopyridine to nicotinamide of the Degussa process is one of the most important commercial processes adopted by some firms in India. However, this process has some disadvantages i.e., the yield of nicotinamide is not very high and the conversion of 3-cyanopyridine is about 99%. Reaction has been conducted at a higher reaction temperature with an appreciable alkali concentration. Nicotinic acid is also produced with nicotinamide in the above process.

U.S. Pat. No. 1,133,013; 1968, describe the catalytic hydration of nitrites by manganese dioxide. Manganese dioxide has been prepared by Redox method using potassium permanganate and manganese sulphate in alkaline medium. The hydration of 3-cyanopyridine has been conducted using catalyst: 3-cyanopyridine mole ratio as 2.16:1, and the yield is only 79.28 mole %. The process i.e., conversion of 3-cyanopyridiae to nicotinamide is similar to the conversion of 4-cyanopyridine to isonicotinamide. Maganese diox has been prepared by Redox method using potassium permanganate and manganese sulphate in alkaline medium. The main drawbacks of the process are that (a) the yield of isonicotinamide is less (b) it is not eco-friendly and (c) the amount of catalyst per mole of the feed for conversion is quite high.

OBJECTS OF THE INVENTION

The main object of the invention is to provide an improved process for conversion of cyanopyridines to nicotinamides.

Another object of the invention is to provide a process for synthesis of nicotinamide from 3-cyanopyridine and isonicotinamide from 4-cyanopyridin using specially prepared Manganese Dioxide as the catalyst which obviates the drawbacks as detailed above.

Yet another object of the invention is to use specially prepared manganese dioxide catalyst of specific characteristics for the hydration of 3- and 4-cyanopyridines to nicotinamide and isonicotinamide respectively with highest conversion and selectivity.

SUMMARY OF THE INVENTION

Accordingly, the invention provides a process for conversion of cyanopyridines to nicotinamides comprising dissolving the cyanopyridine in water; adding a transition metal catalyst prepared in neutral medium, refluxing the reaction mixture, cooling filtering and washing the resultant mixture and evaporating the filtrate to dryness to obtain the product.

In another embodiment of the invention, the refluxing temperature is in the range of 100 to 115° C. and the refluxing time is in the range of 6 to 15 hours.

In one embodiment of the invention, the amount of cyanopyridine dissolved in water is in the range of 0.8 to 2.0 moles for every 1.5 to 8.0 moles of water and the transition metal oxide catalyst is added to in an amount in the range of 0.01 to 0.03 moles.

In another embodiment of the invention, the catalyst used is manganese dioxide.

In another embodiment of the invention, the manganese dioxide catalyst is prepared by a Redox method using potassium permanganate and manganese chloride solution in neutral medium.

In another embodiment of the invention, the product nicotinamide is more than 99% pure confirmed by melting point determination and by FTIR Spectroscopy.

The present invention also relates to a process for preparation of a catalyst useful for preparation of nicotinamide and isonicotinamide which comprises reacting potassium permanganate and manganous salt solution in neutral medium by drop wise addition of aqueous solution of manganous salt to aqueous solution of potassium permanganate with constant stirring, allowing the reaction mixture to stand, filtering the precipitate of $MnO_2$ and washing with distilled water, drying the precipitation to obtain the catalyst.

In one embodiment of the invention, the drop wise addition of aqueous solution of manganous salt to aqueous solution of potassium permanganate is carried out at a temperature in the range of 30 to 80° C. and for a time period in range of 30 minutes to 1 hour.

In another embodiment of the invention, the reaction mixture is allowed to stand for a time period in the range of 10 to 15 hours.

In yet another embodiment of the invention, the precipitate of manganese dioxide is dried in an air oven at 110° C. for 3-4 hours.

In another embodiment of the invention, the manganous salt is selected from manganese chloride and manganese sulphate.

DETAILED DESCRIPTION OF THE INVENTION

It is known to prepare solid oxide catalyst generally by for example, by calcining the hydroxide, to convert it to the corresponding oxide. The hydroxide can be formed in simplest embodiment, by means of normally referred to as precipitation. Such precipitation method comprises adding to an aqueous solution containing as dissolved therein water soluble inorganic or organic salts of manganese, for examples halide, nitrate, sulphate, formate, acetate, oxalate, water soluble basic substance preferably an alkali metal hydroxide, carbonate or bicarbonate such as NaOH, KOH, $Na_2CO_3$, $NaHCO_3$ and ammonium carbonate or bicarbonate to cause the precipitation of the hydroxide, filtering the resulting hydroxide, washing the remaining solid with water and drying the product.

The process steps for preparation of the catalyst consisting of Redox method using an oxidising agent like $KMnO_4$ and a reducing agent like manganous salt i.e. manganese chloride in neutral medium. While the catalyst used in this invention can be prepared by any of the above-described methods, a catalyst prepared by Redox method in neutral medium is preferred.

Manganese dioxide catalyst has also been prepared by other methods i.e. heating $Mn(NO_3)_2 \cdot xH_2O$, by reacting manganese acetate, sulphuric acid and potassium persulphate. Manganese dioxide catalyst prepared by the Redox method using potassium permanganate and manganese chloride in neutral medium showed highest activity and selectivity in the hydration of 3- and 4-cyanopyridines to isonicotinamide. The purity of isonicotinamide is confirmed by determining its melting point and by FTIR Spectroscopy. The maximum yield of isonicotinamide achieved so far is 110-112% (wt. %)(90.2-91.8 mole %).

The present invention also provides a process for preparation of a catalyst useful for the conversion of 3- and 4-cyanopyridines to nicotinamide and isonicotinamide respectively which consists of employing Redox Method using potassium permarganate and manganese chloride solution in neutral medium. The process consists of drop wise addition of aqueous solution of manganese sulphate to aqueous solution of potassium permanganate at a temperature in the range of 70 to 80° C. with constant stirring for a time period in the range of 30 minutes to one hour, left standing for a time period in the range of 10 to 15 hours, filtering the precipitate of $MnO_2$ and washing with distilled water until the filtrate become sulphate free, drying the precipitate in an air oven at 110° C. for three hours; dissolving the cyanopyridines (in the range of 0.8 to 2.0 moles) in water in the range of 1.5 to 8.0 moles; addition of specially prepared manganese dioxide in the range of 0.01 to 0.03 moles; refluxing the reaction mixture at a temperature in the range of 100 to 115° C. for a time period in the range of 6 to 15 hours; cooling, filtering and washing (with water) the resultant mixture and evaporating the filtrate to dryness to obtain the product.

The manganese dioxide is preferably prepared by the Redox method using potassium permanganate and manganese chloride solution in neutral medium. The catalyst so developed for the conversions is an inexpensive, water insoluble transition metal oxide particularly manganese dioxide catalyst of specific characteristics due to generation of more hydroxyl groups characterized by the broad I.R. band in the region 3100-3600 $cm^{-1}$. The separation of the catalyst from the hydration effluent is very much easier.

The product nicotinamide is more than 99% pure, the purity has been confirmed by melting point determination and also by analysing by FTIR Spectroscopy.

Mechanism of hydration using manganese dioxide catalyst is explained as follows:

The role of manganese in the reaction has not yet been elucidated. It may be postulated that since the reaction is bi-phasic, adsorption of the substrate is followed by hydrolysis and subsequent desorption of the product. More easily hydrolysable compounds, are however, those that would be expected to form the most stable carbonium ion, which may perhaps play an important role in the reaction mechanism. The peculiar effectiveness of manganese dioxide may in part be related to the fact that as ordinarily prepared by precipitation it is a 'non-stoichiometric' compound, has oxygen content slightly less than that corresponding to the dioxide and also contains water (3-4%) which cannot be removed thermally without further loss of Oxygen (J. T. Grey, J. Amer. Chem. Sec., 1946,68,605). The water is present probably as hydroxyl group linked to manganese. To confirm this statement, I.R. of different samples of $MnO_2$ prepared by different methods were recorded and in some cases broad band in the region 3100-3600 $cm^{-1}$ were observed indicative of the present of hydroxyl groups. The formation of hydroxylated intermediates may be assisted, if not caused, by these hydroxyl groups in manganese dioxide resulting in the formation of amides.

The novelty of the invention resides in preparing the catalyst manganese dioxide in neutral medium, having 100% selectivity, which is useful for the conversion of 3- and 4-cyanopyridines to nicotinamide and isonicotinamide respectively without use of alkali or acid in comparison to prior art catalysts, which necessitates an extremely complicated and cumbersome separation procedure for the conversion. This catalyst eliminates the formation of nicotinic acid in comparison to prior art.

The following examples are given by way of illustration and therefore should not be construed to limit the scope of the present invention.

EXAMPLE 1

125 ml of 0.471 molar aqueous solution of manganese sulphate was added drop wise to 150 ml of 0.395 molar aqueous solution of potassium permarganate at 80° C. with constant stir for an hour and left standing for 15 hours. The precipitate of $MnO_2$ was filtered and washed with distilled water until the filtrate become sulphate free. The precipitate was dried in an air oven at 110° C. for three hours. Weight of manganese dioxide was observed to be 0.1497 mole.

0.096 mole of 3-cyanopyridine was dissolved in 5.556 mole of water and 0.0115 mole of $MnO_2$, which prepared by above method, was added to this. The mixture was refluxed at 105° C. for 8 hrs. The reaction mixture was cooled and filtered. The filtrate was evaporated in dryness to get solid nicotinamide 0.095 mole. Yield of isonicotinamide was 98.9 mole %.

EXAMPLE 2

115 ml of 0.649 molar aqueous solution of potassium permanganate was added drop wise to 225 ml of 0.5 molar aqueous solution of manganese chloride at 70° C. temperature with vigorous stirring. Addition was continued for 1 hour and kept standing for 15 hours. The precipitate of manganese dioxide was filtered, washed with distilled water to make chloride ion free. The precipitate was put in an air oven at 110° C. for 3 hours and weight of $MnO_2$ was 0.189 mole.

0.096 mole 3-cyanopyridine was dissolved in 4.55 mole of water and 0.0115 mole of $MnO_2$ prepared by above method was added to this. The mixture was refluxed at 100° C. for 13.5 hrs. The reaction mixture as cooled and filtered. The filtrate was evaporated to dryness to get solid nicotinamide 0.0879 mole. Yield of nicotinamide was 91.56 mole %.

EXAMPLE 3

225 ml of 0.332 molar aqueous solution of potassium permanganate was added to 100 ml of 1.125 mole aqueous solution of manganese chloride with continuous stirring at 30° C. The product manganese dioxide was filtered, washed with distilled water till fee from chloride ions. The precipitated manganese dioxide was dried in an air oven at 110° C. for 4 hours. Weight of manganese dioxide was 0.23 mole.

0.096 mole of 3-cyanopyridine was dissolved in 5.556 mole water and 0.0115 mole of manganese dioxide, which was prepared by above method, was added to this solution. The reaction mixture was stirred and refluxed at 100° C. for 8 hours. Reaction mixture was cooled, filtered and washed with distilled water thoroughly. The filtrate was evaporated on a steam bath to dryness. After drying the weight of nicotinamide was 0.0957 mole equivalent to yield of 99.6 mole %.

Comparative Examples for Preparation of MnO2 Using Potassium Permanganate and Manganous Salt in Presence of Sodium Hydroxide

EXAMPLE 4

300 ml of 0.303 molar aqueous solution of manganese chloride and 60 ml 9.75 molar solution of sodium hydroxide was added simultaneously drop wise in the solution of 300 ml of 1.013 molar aqueous solution of potassium permanganate at 70° C. for an hour with constant stirring and kept standing for 12 hrs. The precipitate of manganese dioxide was filtered and washed with distilled water till free from chloride ions. The precipitate was dried at 110° C. for 8 hrs. Yield of manganese dioxide was 0.198 mole.

0.096 mole 4-cyanopyridine was dissolved in 5.556 mole water and 0.0115 mole of manganese dioxide, which was prepared by above method, was added to this. The reaction mixture was refluxed at 100° C. for 8 hrs. in a glycerine bath. The reaction mixture was cooled, filtered and washed thoroughly with distilled water. The filtrate was evaporated on steam bath to dryness. Weight of isonicotinamide was 0.089 mole. Yield was 92.71 mole %.

EXAMPLE 5

0.112 mole of $Mn(NO_3).6H_2O$. was heated by 430° C. for 4 hrs in the muffle furnace 0.107 mole of $MnO_2$ was obtained. The yield of $MnO_2$ was 95.5 mole %.

0.096 mole of 4-cyanopyridine was dissolved in 1.94 mole of water and 0.0115 mole $MnO_2$, which was obtained by above method was added to this and the reaction mixture was refluxed for 8 hours at 115° C. in an oil bath. The reaction mixture was extracted with organic solvent ($CCl_4$). Aqueous layer was evaporated to dryness and yield of isonicotinamide was 0.0082 mole. Unreacted 4-cyanopyridine was 0.048 mole. Yield of isonicotinamide was 8.5 mole %.

EXAMPLE 6

270 ml of 0.332 molar aqueous solution of $MnSO_4.4H_2O$ and 117 ml 10.0 molar aqueous solution of sodium hydroxide were added drop wise simultaneously with constant stirring to hot (at 70° C.) 600 ml of 1.0123 molar aqueous solution of $KMnO_4$. After addition of $MnSO_4.4H_2O$ and sodium hydroxide solution the whole mass was stirred and heated again at 70° C. for 90 minutes. It was kept for settling for 12 hrs. It was filtered and the precipitate was washed several times with distilled water until the precipitate was free from $SO_4^{-2}$ and OH ions. The precipitate was dried in an air oven at 110° C. till constant weight. The yield of $MnO_2$ was 0.314 mole.

0.1923 mole 3-cyanopyridine was dissolved in 7.778 mole of water and 0.023 mole manganese dioxide, which was prepared by above method, was added to this solution. The mixture was refluxed at 100° C. for 8 hrs in a glycerine bath. The reaction mixture was cooled, filtered and washed with distilled water. The filtrate was evaporated on steam bath to dryness. Weight of nicotinamide was 0.165 mole and yield was 85.0 mole %.

The Main Advantages of the Present Invention are

1. Nicotinamide can be produced by catalytic hydration of 3-cyanopyridine without use of alkali or acid as prior art catalyst, which necessitates an extremely complicated and cumbersome separation procedure or the product nicotinamide.
2. The catalyst hydrated manganese dioxide has been prepared by the Redox method using potassium permanganate and manganese chloride solution in neutral medium
3. The catalyst used in the present invention eliminates the formation of nicotinic acid which is produced in substantial amount using the prior art catalysts (acid or alkali).
4. The yield of nicotinamide is 91.8 mole % and the selectivity is 100% which is much higher than the catalyst report so far.
5. The process also provides for easy and economic recovery of nicotinamide from the resulting hydrolysis effluents.

We claim:

1. A process for conversion of a cyanopyridine to a nicotinamide comprising dissolving the cyanopyridine in water; adding a manganese dioxide catalyst prepared by Redox method using potassium permanganate and manganese salt solution in a neutral medium; refluxing the reaction mixture; cooling filtering and washing the resultant mixture and evaporating the filtrate to dryness to obtain the product.

2. A process as claimed in claim 1 wherein the refluxing time is in the range of 100 to 115° C. and the refluxing time is in the range of 6 to 15 hours.

3. A process as claimed in claim 1 wherein the refluxing is carried out for a period in the range of 8-13 hours.

4. A process as claimed in claim 1 wherein the amount of cyanopyridine dissolved in water is in the range of 0.8 to 2.0 moles for every 1.5 to 8.0 moles of water and the transition metal oxide catalyst is added to in an amount in the range of 0.01 to 0.03 moles.

5. A process as claimed in claim 1 wherein the manganese salt is selected from manganese sulphate and manganese chloride.

6. A process as claimed in claim 1 wherein the product nicotinamide is more than 99% pure.

7. A process as claimed in claim 1 wherein the cyanopyridine used is selected from 3-cyanopyridine and 4-cyanopyridine.

8. A process for conversion of a cyanopyridine to a nicotinamide comprising
   dissolving the cyanopyridine in water;
   adding a manganese dioxide catalyst prepared in neutral medium;
   refluxing the reaction mixture at a temperature in the range of 100 to 115° C.;
   cooling filtering and washing the resultant mixture and evaporating the filtrate to dryness to obtain the product.

9. A process as claimed in claim 8 wherein the refluxing time is in the range of 6 to 15 hours.

10. A process as claimed in claim 9 wherein the refluxing is carried out for a period in the range of 8-13 hours.

11. A process as claimed in claim 8 wherein the amount of cyanopyridine dissolved in water is in the range of 0.8 to 2.0 moles for every 1.5 to 8.0 moles of water and the manganese dioxide catalyst is added to in an amount in the range of 0.01 to 0.03 moles.

12. A process as claimed in claim 8 wherein manganese dioxide catalyst is prepared by a Redox method using potassium permanganate and manganese salt solution in a neutral medium.

13. A process as claimed in claim 12 wherein the manganese salt is selected from manganese sulphate and manganese chloride.

14. A process as claimed in claim 8 wherein the product nicotinamide is more than 99% pure.

15. A process as claimed in claim 8 wherein the cyanopyridine used is selected from 3-cyanopyridine and 4-cyanopyridine.

* * * * *